US009265929B2

(12) United States Patent
Ollivier et al.

(10) Patent No.: US 9,265,929 B2
(45) Date of Patent: Feb. 23, 2016

(54) CARDIAC OR CEREBRAL VESSEL MICROLEAD WITH ELECTRODE RING

(71) Applicant: SORIN CRM S.A.S, Clamart (FR)

(72) Inventors: Jean-François Ollivier, Villiers le Bâcle (FR); Nicolas Shan, Juvisy sur Orge (FR); Philippe D'Hiver, Châtillon (FR)

(73) Assignee: SORIN CRM S.A.S., Clamart (FR)

(*) Notice: Subject to any disclaimer, the term of this patent is extended or adjusted under 35 U.S.C. 154(b) by 0 days.

(21) Appl. No.: 13/895,974

(22) Filed: May 16, 2013

(65) Prior Publication Data

US 2013/0310898 A1 Nov. 21, 2013

(30) Foreign Application Priority Data

May 16, 2012 (FR) ...................................... 12 54548

(51) Int. Cl.
*A61N 1/05* (2006.01)
*A61N 1/372* (2006.01)

(52) U.S. Cl.
CPC *A61N 1/05* (2013.01); *A61N 1/056* (2013.01); *A61N 1/0534* (2013.01); *A61N 1/372* (2013.01); *A61B 2562/125* (2013.01); *Y10T 29/49117* (2015.01)

(58) Field of Classification Search
CPC ......... A61N 1/05; A61N 1/372; A61N 1/375; A61B 2562/125
USPC ................... 607/2, 62; 600/372, 381; 128/898
See application file for complete search history.

(56) References Cited

U.S. PATENT DOCUMENTS

| | | | | |
|---|---|---|---|---|
| 4,381,014 A * | 4/1983 | Sandstrom | ............ | A61N 1/056 607/119 |
| 4,835,853 A * | 6/1989 | Hirschberg | ............ | A61N 1/056 219/58 |
| 5,282,844 A * | 2/1994 | Stokes | ................ | A61N 1/0568 607/120 |
| 5,354,327 A * | 10/1994 | Smits | ............................ | 607/116 |
| 5,370,684 A | 12/1994 | Vallana et al. | | |
| 5,387,247 A | 2/1995 | Vallana et al. | | |
| 6,018,684 A | 1/2000 | Bartig et al. | | |
| 6,981,314 B2 * | 1/2006 | Black et al. | ...................... | 29/825 |
| 8,180,425 B2 * | 5/2012 | Selvitelli et al. | .............. | 600/382 |
| 8,382,529 B2 * | 2/2013 | Lim et al. | ...................... | 439/669 |
| 8,442,658 B2 * | 5/2013 | Li | .................................. | 607/122 |
| 8,521,306 B2 * | 8/2013 | Ollivier | ........................ | 607/122 |
| 2003/0143895 A1* | 7/2003 | Sommer et al. | ............... | 439/668 |
| 2005/0113896 A1 | 5/2005 | Pavlik et al. | | |
| 2005/0228469 A1* | 10/2005 | Zarembo | ................ | A61N 1/056 607/122 |
| 2006/0265037 A1 | 11/2006 | Kuzma | | |
| 2007/0043410 A1* | 2/2007 | Boling | .......................... | 607/116 |

(Continued)

FOREIGN PATENT DOCUMENTS

EP 2 455 131 5/2012

*Primary Examiner* — Christopher A Flory
(74) *Attorney, Agent, or Firm* — Foley & Lardner LLP

(57) ABSTRACT

A method of manufacturing a detection/stimulation lead for implantation into a venous, arterial, or lymphatic network is shown and described. The method includes providing a microcable comprising a sheath of insulating material covering an electrically conductive core. The method further includes surrounding a portion of the microcable with an electrically conductive metal ring. The method also includes crimping the ring such that the thickness of the sheath is penetrated by a portion of the metal ring and such that an electrical connection is formed between the metal ring and the electrically conductive core.

16 Claims, 2 Drawing Sheets

(56) References Cited

U.S. PATENT DOCUMENTS

| | | |
|---|---|---|
| 2009/0076356 A1* | 3/2009 | Simpson et al. .............. 600/347 |
| 2009/0134134 A1 | 5/2009 | Wessman |
| 2009/0318999 A1* | 12/2009 | Hall .............................. 607/37 |
| 2009/0326626 A1* | 12/2009 | Swoyer ................ A61N 1/0551 607/116 |
| 2010/0198326 A1* | 8/2010 | Li ................................ 607/119 |
| 2011/0028815 A1* | 2/2011 | Simpson et al. .............. 600/345 |
| 2011/0028816 A1* | 2/2011 | Simpson et al. .............. 600/345 |
| 2011/0065307 A1* | 3/2011 | Conger ......................... 439/430 |
| 2011/0159748 A1* | 6/2011 | Lim et al. ..................... 439/669 |
| 2011/0218603 A1* | 9/2011 | Victorine et al. ............ 607/116 |
| 2011/0277324 A1* | 11/2011 | Conger ......................... 29/863 |
| 2012/0041528 A1* | 2/2012 | Mehdizadeh et al. ........ 607/115 |
| 2012/0053664 A1* | 3/2012 | Hegland et al. .............. 607/116 |
| 2012/0130461 A1* | 5/2012 | Olsen et al. ................... 607/116 |
| 2012/0130464 A1 | 5/2012 | Ollivier |
| 2012/0226177 A1* | 9/2012 | Callahan et al. ............. 600/509 |
| 2012/0271369 A1* | 10/2012 | Ollivier ........................ 607/4 |
| 2013/0338745 A1* | 12/2013 | Ollivier et al. ............... 607/116 |
| 2014/0107455 A1* | 4/2014 | Regnier et al. ............... 600/381 |
| 2014/0163659 A1* | 6/2014 | Boling ......................... 607/116 |

* cited by examiner

CARDIAC OR CEREBRAL VESSEL MICROLEAD WITH ELECTRODE RING

CROSS-REFERENCE TO RELATED APPLICATIONS

The present application claims the benefit of and priority to French Patent Application No. 1254548, filed May 16, 2012, under 35 U.S.C. §119. The entirety of French Patent Application No. 1254548 is incorporated herein by reference.

BACKGROUND

The present application relates generally to the field of "active implantable medical devices" as defined by Directive 90/385/EEC of 20 Jun. 1990 the Council of the European Communities. The present application more specifically relates to a detection/stimulation microlead intended to be implanted in venous, arterial or lymphatic networks. Such a lead can be used in cardiology (e.g., to be implanted in the coronary sinus vein to stimulate a left or right cavity of the heart). Further, microleads are often useful in many other medical applications, including applications where there is the presence of a venous, arterial or even lymphatic network, including the venous or arterial cerebral network.

Electrical stimulation has led to major advances in neurology in the field of neuromodulation (e.g., a technique to stimulate target areas of the brain for the treatment of disorders such as Parkinson's disease, epilepsy and other neurological diseases). Such a technique often allows a less invasive approach of these treatments and especially superior efficacy of treatments.

It is challenging and difficult to provide stimulation microleads of very small diameter but which are nevertheless extremely robust to provide long-term biostability.

While the size of current implantable leads is typically on the order of 4 to 6 French (1.33 to 2 mm), it would be desirable to reduce the diameter to less than 2 French (0.66 mm). Such a size of microlead could access small veinlets, inaccessible today with larger devices. Such a microlead must also be able to easily navigate through the venous arterial or lymphatic networks with sufficient flexibility to be introduced into vessel networks with high tortuosity, anastomosis, etc.

However, in the prior art, the reduction in lead diameter often increases technological complexity and imposes technical constraints generating risks.

Conventional microleads can include a central conductor for connection to the generator of the implant. The conductor can be coated with an electrically insulating sheath. Such microleads typically include an active portion including one or more detection/stimulation electrodes electrically connected to the central conductor and intended to come into contact with the target vessel wall.

In the prior art, a first production technique of the electrodes for a microlead includes stripping the insulating sheath so as to expose the microcable at one or more points. The stripped points together constitute a network of electrodes connected in series (monopolar lead configuration), allowing multiple points of stimulation and thus providing multizone dissemination of the stimulation energy delivered by the implant. Such a technique is described, for example, in the EP2455131 and US2012/0130464. These applications also, in an alternative embodiment, disclose production of the active part of the microlead by successively and alternately threading on the microcable insulating tubes and short conductive electrodes of platinum-iridium, in the form of rings. The insulating tubes, made, for example, of polyurethane, are affixed to the microcable and the platinum-iridium electrodes are crimped directly to this microcable.

Another technique for forming electrodes on a microcable can include applying a coating to the microcable polyurethane adhesive, leaving locally appearing conductive uncoated surfaces. With techniques that include the exposure of microcable (removal of the insulation or surfaces left in reserve), it is sometimes needed to provide a conductive coating (e.g., an alloy of titanium nitride or a carbon deposit, such as Carbofilm) by a sputtering technique such as described in, e.g., US5370684 and US5387247, to protect the exposed cable to corrosion. Such a coating can be made of an alloy such as MP35N (35% Ni, 35% Co, 20% Cr and 10% Mo) (e.g., considered stainless under standard conditions). However, in certain circumstances, such a material can be relatively sensitive to electrocorrosion—e.g., a corrosion phenomenon accentuated by the current flow in the polar regions (electrodes) and by contact with surrounding body fluids (blood, etc.).

Applicants have identified a need for reducing the risk of infusion of corporeal fluids to the microcable. The microcable can be completely isolated from any contact with the environment of the microlead, hence the additional conductive coating of titanium nitride NiTi or carbon on the electrode areas or the crimping on the microcable of platinum-iridium rings (noble material, resistant to corrosion). This constraint of isolation of the microcable with the external environment, particularly in the region of the electrodes should ideally be respected i) throughout the expected life of the microlead, ten years, and ii) throughout all the mechanical movements of the microlead (e.g., 400,000,000 bending stresses without breaking—corresponding to the average number of heart beats on the life of the microlead). The fulfillment of these conditions is desirable for a microlead intended to be implanted in the body (e.g., in a coronary vessel). A stimulation microlead in the venous system may experience localized of deformation under curvatures much higher than those experienced by a conventional lead, since it must follow the deformation of the veins. This can cause higher microlead stresses than some other application.

U.S. 2009/134134 A1 discloses a lead structure comprising a ring electrode (i.e., band electrode) connected to a coiled conductor embedded in the thickness of the hollow sheath of the lead body. The insulating sheath is locally stripped to discover the conductor, and a ring is welded to the latter for the electric connection. However, in such a lead, the risk of long-term infusion of body fluids toward the conductor remains because no specific mechanism of protection of the joints or isolation of the conductor with the environment of the microlead is provided. U.S. 2006/265037, U.S. 2005/113896, and U.S. Pat. No. 6,018,684 each describe other structures of ring electrodes, having the same drawback.

SUMMARY

The problem of the invention is to provide a microlead in which the function of protection barrier against the microcable electrocorrosion at the electrodes can be provided under the conditions described above.

The invention may provide a method of manufacturing of a detection/stimulation lead. The method can include obtaining a conductor with a sheath of electrically insulating polymeric material covering the conductor on its periphery and on its length, the outer diameter of the assembly being at most equal to 2 French (0.66 mm). The method can further include obtaining at least one detection/stimulation electrode formed by a metal ring. The ring can include two end portions extending in the longitudinal direction on either side of a central part, and making of a contact of the conductor with the ring.

The step of making a first contact of the conductor with the ring can include crimping of the ring on the conductor. The conductor can be a full core microcable which is surrounded by said sheath of electrically insulating polymer material. Crimping is performed in a substantially non-stripped area of the microcable and is conducted on the central part of the ring so as to: i) clamp the sheath between the ring and the microcable ii) locally penetrate the thickness of the sheath with an area of the internal side of the ring, so as to bring into mechanical and electrical contact the ring with the microcable in at least one puncture area of the sheath, and, iii) push the insulating material in areas adjacent to said puncture area of the sheath such that the insulating material of the sheath remains interposed between the microcable and the ring in regions on both sides of said puncture area of the sheath.

According to a second aspect, the invention provides a detection/stimulation lead produced by implementation of the above method.

This lead can include a conductor adapted to be connected to a generator of an active implantable medical device, a sheath of electrically insulating polymer material covering the conductor on its periphery and along its length, and at least one detection/stimulation electrode formed by a metal ring electrically connected to the conductor, designed to come into contact with the wall of a target vessel of said venous, arterial or lymphatic network. The outer diameter of the lead can be at most equal to 2 French (0.66 mm). The ring includes two end parts extending in the longitudinal direction on either side of a central portion. In the central portion, the inner face of the ring can be in mechanical and electrical contact with the conductor surface in at least a puncture area of the sheath, while the inner side of the end portions of the ring is in mechanical contact with the surface of the sheath. In other words, the insulating material of the sheath can remain between the conductor and the ring in regions on both sides of said at least one puncture area of the sheath.

The conductor may be a full core microcable surrounded by a sheath of electrically insulating polymeric material. The ring may be disposed on the microcable in a substantially unstripped region thereof. Only after crimping, in other words, does the microcable have at least one puncture area in the sheath (e.g., corresponding to the central portion of the ring). The insulating material may be interposed between the ring and the microcable in areas adjacent to said at least one puncture area of the sheath.

The puncture area of the sheath may be a continuous circumferential area and located in a plane that is perpendicular to the sheath axis. The puncture area of the sheath, in other embodiments, may be a discontinuous circumferential area, also located in a plane that is perpendicular to the sheath axis, with a plurality of puncture areas of the sheath leaving between them areas of continuous insulation connecting the two portions of the sheath located either side of the ring. The ring can include, on its inner face, at least one projection adapted to define a puncture area of the corresponding sheath. The projection may be either a relief including a longitudinal profile homologous to that of a tool's crimping jaws, without extra thickness of the ring at that location, or a relief including an extra-thickness formed on the inner or outer side of the ring. In the longitudinal direction, in some embodiments, the relief may not extend to the end of the ring. The ring may carry, on its inner face, a plurality of grooves having helical straight and/or longitudinal portions. The ring may carry, on its outer face, longitudinal reinforcing ribs. The wall thickness of the ring may be between 20 and 100 µm. The length of the ring may be between 0.5 and 1.5 mm. The material of the ring may be an alloy of platinum-iridium or palladium, and the surface material of the microcable is an alloy such as MP35N or MP35NLT. The wall thickness of the sheath may be between 5 and 50 µm. The electrically insulating polymeric material of the sheath may be selected from the following group: polyurethanes (PU), polyester (PET), polyamide (PA), polycarbonates (PC), polyimides, fluorinated polymers, polyether-ether-ketone (PEEK), poly-p-xylylene (parylene), polymethyl methacrylate (PMMA), PTFE (polytetrafluoroethylene), FEP (perfluorinated propylene), PFA (perfluoroalkoxy copolymer resin), THV (tetrafluoroethylene, hexafluoropropylene, vinylidene fluoride), PVDF (polyvinylidene fluoride vinylidene), EFEP (ethylene propylene fluorinated ethylene) and ETFE (ethylene tetrafluoroethylene). An electrode structure for a monopolar detection or stimulation microlead of the present invention may be implanted in a cardiac or cerebral vessel.

The microlead may include a microcable 18, a insulating sheath 20 and at least one detection/stimulation electrode electrically connected to the center conductor of the microcable 18. The microlead may have an outer diameter of at most equal to 2 French (0.66 mm). The active electrode may be formed by a metal ring 22 crimped onto the microcable in an area not previously exposing the conductive core. In the central part 24 of the ring, its internal face forms a mechanical and electrical contact connection with the surface of the microcable 18 in a puncture area of the sheath 20. The insulating material may be pressed to areas 30 adjacent the puncture area. In the end portions 26 of the ring, its internal face provides a mechanical connection contact with the surface of the sheath 20. The insulating material of the sheath 20 may be interposed between the microcable 18 and the ring 22 in regions 30 located on either side of said one puncture area of the sheath 20.

A method of manufacturing a detection/stimulation lead for implantation into a venous, arterial, or lymphatic network is shown and described. The method includes providing a microcable including a sheath of insulating material covering an electrically conductive core. The method further includes surrounding a portion of the microcable with an electrically conductive metal ring. The method also includes crimping the ring such that the thickness of the sheath is penetrated by a portion of the metal ring and such that an electrical connection is formed between the metal ring and the electrically conductive core.

DETAILED DESCRIPTION

Figure 1:
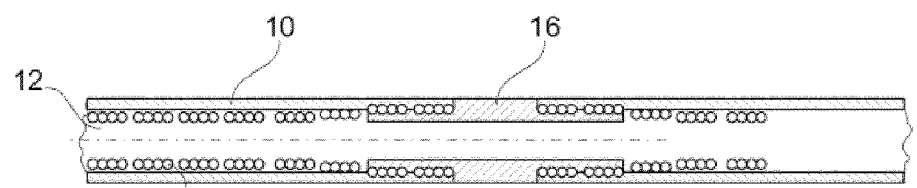
FIG. 1 shows a longitudinal section of a typical structure of the electrode of a monopolar lead of the prior art.

FIG. 1 is an illustration of one prior art lead, shown schematically in a sectional view. A conventional monopolar stimulation electrode is shown. This conventional construction includes an electrically insulating lead body 10, with a central lumen 12 for the introduction of a guide wire used for the implantation of the lead. The internal region of the lead includes a coiled conductor 14 (typically made of an alloy such as MP35N) electrically connected to an electrode 16 (typically made of a PtIr alloy) mounted on the lead body 10. Given the size constraints of the guide wire thickness and the insulation thickness, the diameter of such a conventional lead is generally between 4 and 8 French (1.33 and 2.66 mm). The presence of electrode 16 introduces a discontinuity in the structure of the lead that may have an impact on the long-term endurance of the lead (e.g., particularly in the case of inadequate design/fitting of the different elements).

Figure 2:
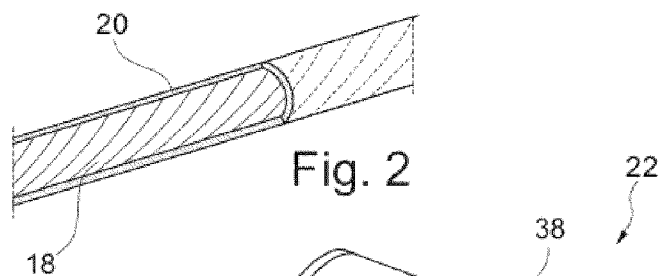
FIG. 2 illustrates the structure of the isolated microcable used in the microlead of the present invention, according to an exemplary embodiment.

Referring now to FIG. 2, the present invention can advantageously provide a microlead having a diameter which does not exceed 2 French (0.66 mm). In an exemplary embodiment of the present invention, a microlead includes a wrapped microcable such as that illustrated in FIG. 2. The wrapped microcable of FIG. 2 is shown to include a core microcable 18 formed of a solid central conductor, surrounded by an insulating layer 20. The assembly can have an overall diameter of equal to or less than 2 French (0.66 mm) and may typically have an overall diameter of about 0.5 to 2 French (0.17 to 0.66 mm).

The microcable can be made of an alloy such as MP35N or MP35NLT, or another material having an advantage of high fatigue endurance. The microcable of FIG. 2 is advantageously a multi-stranded structure. In other words, the core strand 18 is formed of a plurality of conductive strands of small diameter. The reduction in diameter of the individual strands can make it possible to reduce the stress applied to each strand, and thus to increase the fatigue performance of the structure of the complete core 18. In some embodiments the microlead of FIG. 2 does not include an internal lumen and, with several microwires twisted together, is capable of both endurance against cardiac movements and resistance to stress related to the implantation.

The implantation of such a microcable with no internal lumen may require the prior permanent implantation of an implantable body lead. In such a process, the surgeon uses a main catheter allowing access at the entry of the coronary sinus, and a sub-selection catheter to choose (with the use of an image intensifier) the path of the venous system that will achieve the target vein corresponding at the selected stimulation site. The surgeon then inserts a guidewire into the catheter, that he/she pushes forward to expose it in the coronary venous system in order to select a particular collateral vein. Once the vein is selected, the surgeon introduces the lead body on the guidewire, and makes it slide and progress on the guide wire to the desired location. After removal of the guidewire, the microcable is pushed into the lead body from the proximal end thereof, and it is pushed along the entire length of the lead body to emerge from the outlet of the proximal end thereof, and then is deployed beyond so as to make it progress, under an image intensifier, in the collateral veins until it reaches the desired position. It is thus possible to reach and stimulate areas of the venous coronary network previously inaccessible with conventional leads. These microcable structures are available for example from the Fort Wayne Metals Company Inc., Fort Wayne, USA, and are used in the medical field in particular to manufacture defibrillation conductors.

Regarding the insulating layer 20, in some embodiments it is: relatively fatigue resistant, electrically isolated, long-term biocompatible, biostable, and suitable for use with the conductor of the core cable. The materials that can be used for the insulating layer include the materials of the group including: polyurethanes (PU), polyesters (PET), polyamides (PA), polycarbonates (PC), polyimides, fluorinated polymers, polyether ether-ketone (PEEK), poly-p-xylylene (parylene) and polymethyl methacrylate (PMMA). In some embodiments the insulating layer is a material or a combination of materials having relatively high chemical inertness such as of fluoropolymers, which also have very good insulation. Such materials or compounds may include: polytetrafluoroethylene (PTFE), FEP (perfluorinated propylene), PFA (copolymer resin perfluoroalkoxy) HSR (tetrafluoroethylene, hexafluoropropylene, vinylidene fluoride), PVDF (polyvinylidene fluoride), the EFEP (ethylene fluorinated ethylene propylene) and ETFE (ethylene tetrafluoroethylene).

The particular methods for producing the insulating layer of the core microcable may depend on the materials used, for example: co-extrusion on the conductor (for PU, PA, PEEK, polyimides and fluorinated polymers); deposition by soaking in a solution (for PU, PA and polyimides); heating of a heat shrinkable tube (for PET and fluoropolymers); chemical deposition using a gas (for parylene); and plasma processing to improve adhesion between the layers.

Although FIG. 2 has been illustrated with a single layer of the same material sheathing the microcable 18, it is possible to provide several layers forming the sheath 20 of microcable, e.g. a PET layer and an ETFE layer.

An active microlead is provided with one or more electrodes for detection and/or stimulation. The electrode or electrodes are electrically connected to the central conductor.

Figure 3:
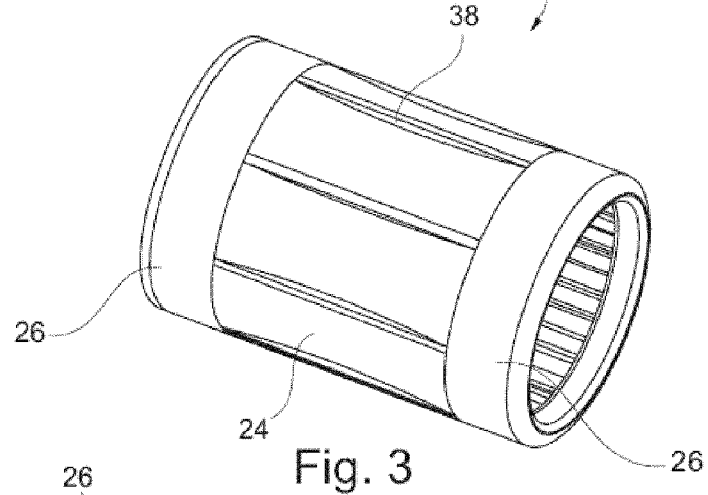
FIG. 3 shows in perspective an example of a crimping ring for the production of a detection/stimulation electrode, according to an exemplary embodiment.

Referring now to FIG. 3, the solution proposed by the invention is to crimp a ring 22 on the microcable. The ring can be made of a material not subjected to electrocorrosion such as a platinum-iridium alloy (typically 90/10) or of another noble metal such as palladium or tantalum, insensitive to the phenomenon of electrocorrosion.

The length of the ring in the longitudinal direction may be 0.5 to 1.5 mm. The ring may have a diameter of about 2 French (0.66 mm).

The crimping of the ring may be completed directly on the microcable in an area not exposing the conductive core. The crimping can be conducted to very locally pierce the thickness of the insulating sheath 20. The local piercing can occur when the sheath is clamped between the ring and the microcable. The crimping and the resulting piercing can establish a physical and electrical contact between the inner face of the ring 22 and the conductive material of the microcable 18. The resulting structure obtained after crimping is shown in FIG. 4, according to an exemplary embodiment.

Figure 4:
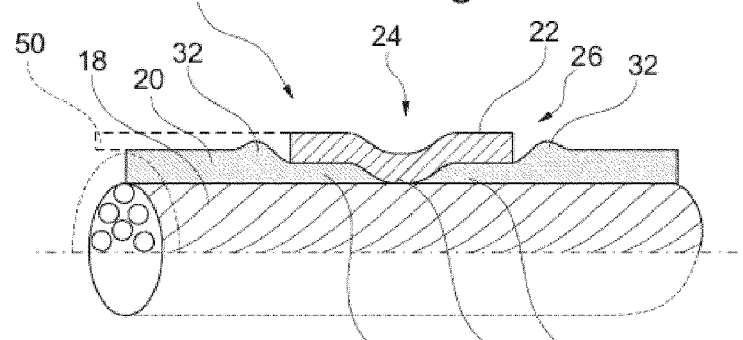
FIG. 4 is a longitudinal section of an electrode structure for a monopolar lead, which may be formed by crimping a ring such as that in FIG. 3 on the microcable in FIG. 2, according to an exemplary embodiment.

Referring to FIGS. 3 and 4, on the central portion 24 of a ring which has locally been crimped (e.g., as shown in FIG. 4), the ring has a smaller diameter (as a result of crimping) relative to the end portions 26 located on either side of this central portion 24. This geometry may result from differential crimping of the ring, with a force greater in the central part 24 than in the end portions 26. This creates, on the one hand, the electrical contact in the area 28 in the center of the ring where the insulating material 20 is pierced. On the other hand, areas of compression 30 of the insulating material 20 at both terminations of the ring may purposefully be pushed (i.e., bunched, compressed, etc.). These areas 30 can assist in providing a seal protecting the microcable 18 of electrocorrosion (during crimping the sheath material may be pushed from the zone 30 outwardly to 32, near the end regions of the ring).

With greater particularity regarding the crimping, at the central portion 24, the inner surface of the ring 22 comes into mechanical and electrical connection contact with the outer surface of the strands on the surface of the microcable core. This connection contact occurs in the piercing or puncture area 28 of the insulating material 20. The contact resistance obtained can be very low, e.g., less than 1Ω, and stable. At the end regions 26 of the ring 22, the inner face of the ring is in mechanical connection contact with the surface of the sheath. In some embodiments, the end regions 26 do not pierce the sheath material. In other words, at the end regions 26, material is interposed between the microcable 18 and the ring 22. The material 30 of the sheath may be pushed away from the ring (e.g., by creeping during crimping) and may act as a seal, forming an insulating barrier between the external environment and the electrical contact area (puncture area 28). The material of the microcable is therefore protected, thus preventing penetration of body fluid to the region 28 of the electrical contact.

In order to support electrical contact achieved by direct crimping of the ring 22 to the microcable 18 coated with its sheath 20, the wall thickness of the ring may be relatively low, of the order of 20 to 100 μm, typically 25 μm, depending on the crimping constraints to easily allow sufficient deformation (e.g., without breaking the ring).

As for the sheath 20, its thickness may be selected in the range of 5 to 50 μm in order to puncture easily. In addition, the material of this jacket may be chosen to be relatively sensitive to creep, so as to be punctured as soon as the contact pressure (resulting from the crimping force) is high enough. Materials such as ETFE, PET can meet this requirement, in addition to their excellent biocompatibility and resistance to fatigue in the long term.

Certain embodiments include various improvements to the above-described method of connection of the ring to the microcable.

Figures 5A, 5B:
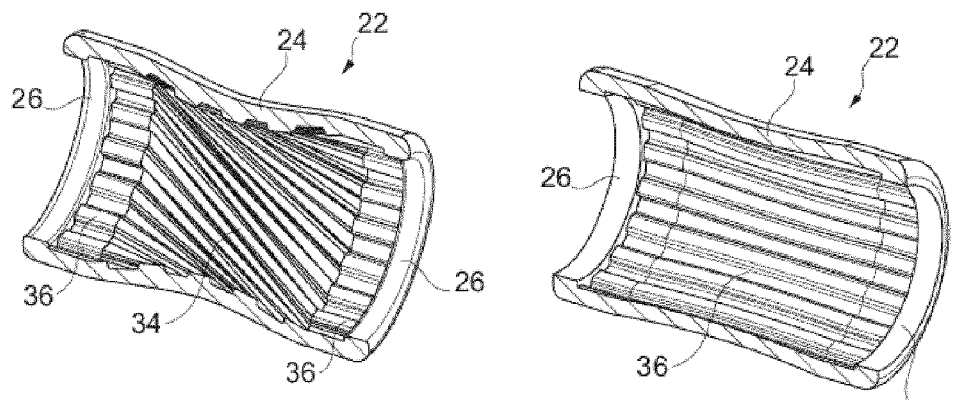
FIGS. 5a and 5b are cut-away perspective views of the electrode ring to be crimped, showing two possible configurations of internal grooves, according to various exemplary embodiments.

As shown in FIGS. 5a and 5b, the rings are shown (in the not crimped state) as having a variable longitudinal profile to the inner lumen of the ring, defining a smaller diameter in the central part 24 than in the end parts 26. This shape may help facilitate the puncturing of the insulation in the central part 24 with a simple crimping tool having a constant longitudinal profile. As shown in FIGS. 5a and 5b, respectively, the overall reduction of the internal diameter in the central part of the ring 24 may be supplemented by a series of helical (34) and/or straight (36) internal grooves whose function is to promote the local puncturing of the insulation layer in the central portion. In both FIGS. 5a and 5b the end portions 26 are smooth and cylindrical.

It is also possible, as shown in FIG. 3, to increase the outer diameter with a series of longitudinal ribs 38 of small thickness, to maintain the inner preshape during crimping.

Figure 6A:
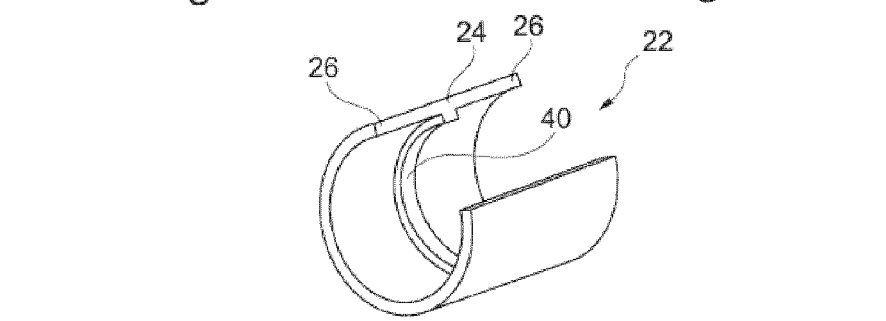
FIGS. 6a, 6b and 6c are schematic perspective cut-away views showing three possible embodiments of reliefs formed on the inner wall of the ring electrode, according to various exemplary embodiments.
Figures 6B, 6C:
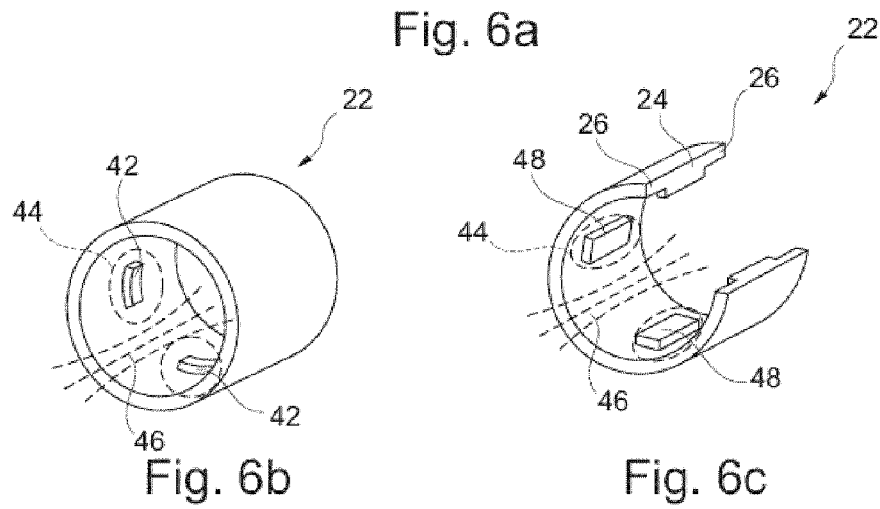

FIGS. 6a, 6b and 6c illustrate embodiments in which the differential crimping (between the central portion 24 and the end portions 26) is not the result of a non-uniform longitudinal profile of the crimping jaws acting on the ring, and/or of a specific profile of the ring, but of the presence of one or more reliefs on the inner face of this ring, which can then maintain a straight external profile. Alternatively or in addition, one or more of such reliefs can be formed on the outside of the ring.

In the example of FIG. 6a, the internal relief 40 is a continuous circumferential relief, while FIGS. 6b and 6c illustrate discrete reliefs such as 42 or 48.

In the latter case, each relief defines around it a puncture zone 44 of the insulating layer, the successive puncture areas 44 being separated from each other by intermediate zones 46 wherein the insulation has not been crossed. "Straps" of intact insulating material are thus formed connecting the terminations of the ring, which has the effect of providing the insulating sheath with better fatigue endurance, due to the mechanical continuity of the sheath on the entire length of the microlead, including the electrodes.

Resistance to electrocorrosion of the microcable/electrode interface can be enhanced by providing the strands constituting the microcable 18 of a coaxial bi-material structure with a core strand in an alloy such as MP35 associated with a coating of a layer of noble alloy, e.g., Pt—Ir, naturally protected against corrosion even in the event of accidental infiltration of body fluid.

Finally, to give the microlead its "isodiameter" characteristic, the assembly having the microcable 18, sheath 20 and provided with crimped rings 22 can be supplemented by additional heat shrink tubing 50 (FIG. 4) disposed on both sides of each electrode. This heat shrink tubing has the double advantage of i) giving the microlead finished state a preshape (curvature imposed during thermoforming) and ii) compensating the slight thickness due to the crimping of the rings 22 on the microcable.

Applicants respectfully submit that some embodiments of the invention may include one or more of the following advantages. Ease of implementation: A prior art production step of ablating portions of the insulation layer is avoided, such step presenting significant risks of damage of the microcable. Protection against infusion of body fluids to the microcable: During crimping the insulation is pushed close to the points of physical contact, while enhancing the sealing of this zone, and avoiding use of a deposit of silicone or polyurethane glue, which would be very difficult to perform given the very small size of gaps to fill (residual spaces between the microcable and the crimped ring). Adding heat shrink tubing provides a possibility of obtaining an isodiameter profile (maintaining the structural mechanical continuity of the product, due to the continuity of the microcable, which is not interrupted as in conventional leads). Because of its short length, the addition of the ring does not significantly alter the natural radius of curvature of the microcable due to its own rigidity under a constraint mode corresponding to normal conditions (minimum radius of curvature of the order of 4 mm, for a length of ring between 0.5 and 1.5 mm). To the extent the crimping slightly modifies the profile of the cylindrical outer surface of the ring, this can have the effect of locally densifying the outward current (peak effect electric), with a consequent reduction in the pacing threshold and with a corollary benefit of a corresponding reduction of energy consumed by the system.

What is claimed is:

1. A method of manufacturing a detection/stimulation lead for implantation into a venous, arterial, or lymphatic network, comprising:
    providing a microcable comprising a sheath of insulating material covering an electrically conductive core;
    surrounding a portion of the microcable with an electrically conductive metal ring;
    crimping the ring to achieve a differential crimping profile wherein the inner diameter of at least a central longitudinal portion of the conductive metal ring is smaller than the inner diameter of the longitudinal end portions on either side of the central portion, and such that the thickness of the sheath is penetrated by a portion of the metal ring and such that an electrical connection is formed between the metal ring and the electrically conductive core without removing insulating material at the penetration location; and while crimping the ring, pushing insulating material beneath the metal ring to areas adjacent the edges of the metal ring to provide a seal.

2. The method of claim 1, further comprising:
continuing the crimping until the sheath penetration creates a puncture area in the sheath which is a continuous circumferential region and located in a plane perpendicular to the axis of the microcable and sheath.

3. The method of claim 1, further comprising:
discontinuing the crimping before the sheath penetration results in a continuous circumferential region.

4. The method of claim 3, further comprising:
forming a plurality of puncture areas of the sheath via the crimping, leaving areas of continuity of insulation between sheath parts located on either side of the ring.

5. The method of claim 4, further comprising:
forming the ring to include at least one interior relief adapted to define a puncture area of the corresponding sheath.

6. The method of claim 5, wherein said relief comprises a longitudinal profile positioned to share an elongated axis with the microcable.

7. The method of claim 6, wherein said relief comprises a thickened portion formed on an interior or exterior surface of the ring.

8. The method of claim 7, wherein, in a longitudinal direction, said relief does not extend up to an edge of the ring.

9. The method of claim 1, further comprising:
forming the ring to include a plurality of grooves on the ring's inner face.

10. The method of claim 9, wherein the plurality of grooves comprise helical grooves.

11. The method of claim 1, wherein the wall thickness of the ring is between 20 and 100 µm, wherein the length of the ring is between 0.5 and 1.5 mm, wherein the wall thickness of the sheath is between 5 and 50 µm, and wherein the material of the ring comprises an alloy of platinum-iridium or palladium.

12. The method of claim 1, wherein the surface material of the microcable comprises an alloy of the group: MP35N or MP35NLT.

13. The method of claim 1, wherein the sheath comprises an electrically insulating polymer material selected from the following group: polyurethanes (PU), polyester (PET), polyamides (PA), polycarbonates (PC), polyimides, fluoropolymers, polyether-ether-ketone (PEEK), poly-p-xylylene (parylene), polymethyl methacrylate (PMM), PTFE (polytetrafluoroethylene), FEP (perfluorinated propylene), PFA (perfluoroalkoxy copolymer resin), THV (tetrafluoroethylene, hexafluoropropylene, fluoride vinylidene), PVDF (polyvinylidene fluoride), EFEP (ethylene fluorinated ethylene propylene) and ETFE (ethylene tetrafluoroethylene).

14. The method of claim 1, wherein the differential crimping profile is achieved by crimping the electrically conductive metal ring to penetrate the sheath, wherein the ring is locally crimped with a greater force at the central portion of the ring than at the end portions on either side of the central portion.

15. The method of claim 1, wherein the differential crimping profile is achieved by crimping the electrically conductive metal ring to penetrate the sheath, wherein the ring comprises a variable longitudinal profile on the inner surface of the ring defining a smaller diameter in the central portion than at the end portions on either side of the central portion, and crimping the ring with a crimping tool having a constant longitudinal profile.

16. The method of claim 1, wherein the differential crimping profile is achieved by crimping the electrically conductive metal ring to penetrate the sheath, wherein the ring comprises one or more reliefs on the inner surface of the ring, the one or more reliefs creating a portion of the inner surface having a reduced diameter.

* * * * *